United States Patent [19]

Kaplan et al.

[11] 4,155,868

[45] May 22, 1979

[54] ENZYME AND ACTIVE OXYGEN CONTAINING DENTURE CLEANSER TABLET

[75] Inventors: Leonard L. Kaplan, East Brunswick; Norman A. Levin, Somerville, both of N.J.

[73] Assignee: Johnson & Johnson, New Brunswick, N.J.

[21] Appl. No.: 773,621

[22] Filed: Mar. 2, 1977

Related U.S. Application Data

[63] Continuation of Ser. No. 643,044, Dec. 22, 1975, abandoned.

[51] Int. Cl.$^2$ .................... C11D 3/395; C11D 7/54
[52] U.S. Cl. ........................................ 252/95; 252/94; 252/99; 252/DIG. 12; 424/53
[58] Field of Search ............. 252/94, 95, 99, DIG. 12; 424/53

[56] References Cited

U.S. PATENT DOCUMENTS

| | | | |
|---|---|---|---|
| 2,931,776 | 4/1960 | Howard | 252/99 |
| 3,607,759 | 9/1971 | Barth | 252/99 |
| 3,630,924 | 12/1971 | Miller | 252/95 |
| 3,855,142 | 12/1974 | Pader et al. | 252/DIG. 12 |
| 3,976,601 | 8/1976 | Levin | 252/99 X |

*Primary Examiner*—Mayer Weinblatt
*Attorney, Agent, or Firm*—Steven P. Berman

[57] ABSTRACT

A completely water soluble effervescent denture cleanser tablet containing both an enzyme and one or more active oxygen compounds. The enzyme in said tablet is resistant to premature inactivation by the oxidizing agents in the tablet during storage and in use and therefore has the added enzymatic cleansing power not possessed by conventional tablets containing only the active oxygen compounds. A method for preparing enzyme-containing denture cleanser tablets in which the activity of the enzyme is usefully retained is also described.

9 Claims, No Drawings

4,155,868

ENZYME AND ACTIVE OXYGEN CONTAINING DENTURE CLEANSER TABLET

This is a continuation of application Ser. No. 643,044 filed Dec. 22, 1975, now abandoned.

DESCRIPTION OF THE INVENTION

This invention relates to denture cleanser tablets and, more particularly, is directed to an improved completely water-soluble denture cleanser tablet containing enzymatic cleansing agents.

Dentures may be cleansed either by immersion in a cleansing solution or by brushing with a cleansing agent in the manner of natural teeth. The former method is generally a preferred method, partly from the standpoint of convenience but also where dentures are of plastic, brushing tends to mar the smooth surfaces. Cleansing solutions may be preformed liquid solutions but for storage convenience are usually in the solid form and the cleansing solutions prepared at the time of use by dissolving the solid cleanser in tap water. The solid cleanser may be in the form of loose powder or granules or may be in the form of tablets. The tablet form is the preferred form since loose granular or powdered forms, even where premeasured, is subject to spillage and loss, and is further subject to possible inhalation and contact with the skin which should be avoided because of the toxic, alkaline or other hazardous nature of the cleansing agents.

The usual denture cleanser tablets have, as primary active cleansing agent, one or more peroxygen or active oxygen compounds such as sodium perborate monohydrate, sodium perborate tetrahydrate, potassium persulfate, sodium carbonate peroxide and the like, which cause the tablets to evolve microbubbles of nascent or active oxygen as they are dissolved in water and provide an oxidizing cleansing action including a bleaching effect on denture stains. Frequently, a hypochlorite ion forming oxidizing agent is also included to provide additional oxidizing cleansing action. Usually it is dichloroisocyanuric acid or its alkali metal salt but it may be sodium chloride which in the presence of peroxygen compound forms hypochlorite. Generally, a minor amount of surfactant is also added to lower the surface tension and to enhance the cleansing action.

Denture cleanser tablets also contain an effervescence producing composition consisting of acids, such as citric and tartaric acids or acid phosphates and a carbonate such as sodium bicarbonate, the interaction of which generates carbon dioxide bubbles as the tablet dissolves when it is placed in water, thereby providing a mechanical cleansing action as well as aid to the disintegration of and the complete dissolution of the tablet. Usually, to prevent the generated carbon dioxide bubbles from adhering to the dissolving tablet and hindering the solvent action of the water, they may contain an anti-foam silicone such as dimethyl polysiloxane.

In addition, denture cleanser tablets usually contain various other relatively inactive ingredients such as fillers, extenders, binders, indicators or dyes and flavors, etc. Formulations for denture cleanser tablets also contain a lubricant system which is incorporated to facilitate smooth and even flow of the dry granular materials of the formulations during tabletting operations.

The desirability of adding enzymes to denture cleanser tablets has been recognized. Food materials, mucin which is primarily a glycoprotein, and plaque which is primarily protein but also carbohydrate in nature may be attacked by appropriate enzymes. Plaque matrix composed of salivary proteins, bacterial cells, polyglucans, etc. tend to retain highly colored materials such as berry, grape, tea, coffee and tobacco stains because they are embedded or "locked into" the plaque matrix. Certain stains, particularly berry and grape stains are particularly tenaciously held and therefore difficultly removed. Although it would be desirable to incorporate enzymes in tablets, useful incorporation has not been accomplished heretofore because of the inactivating effect of active oxygen compounds when compressed with the enzyme. Moreover, certain combination of ingredients are not tabletable. Because of this, enzymes in denture cleanser tablets have not previously been realized successfully and tablets containing enzymes are not readily available. In addition, since the enzyme is rapidly deactivated by the active oxygen compound when the composition is placed in water for use, tabletting is avoided. Although denture cleanser compositions which include dextranase or lipase in the composition are disclosed in U.S. Pat. Nos. 3,630,924 and 3,855,142 respectively, non-tablet cleansing compositions are illustrated and it is not shown how a proteolytic enzyme or any enzyme may be usefully incorporated in a tablet containing an active oxygen compound.

It is desirable therefore to provide for a denture cleanser in tablet form which will supply an enzymatic cleansing action not only to attack the food materials that are loosely bound to the mucin and plaque but preferably to attack the protein of the plaque mixtrix thereby removing the adhering and embedded stains, particularly stubborn stains such as berry and grape while at the same time providing the oxidizing, bleaching and other cleaning functions usually provided by readily available tablets.

According to the present invention, there is provided a water-soluble denture cleanser in tablet form comprising an enzyme and at least one active oxygen compound in an effervescent composition in which each of the cleansing functions, namely the enzymatic, the oxidizing and the mechanical cleansing actions are usefully effective. The tablet is resistant to premature inactivation of the enzyme by the oxidizing agent in storage and in use. Thus, in the tablets of the present invention the retention of the usefully effective enzymatic cleansing activity provides not only for superior cleansing but also for accomplishing it in a shorter time than heretofore possible.

The denture cleanser tablet of the present invention is a single layered tablet in which an enzyme, active oxygen compounds and an effervescence producing composition, provide for the enzymatic, oxidative and mechanical cleansing functions respectively, are incorporated in such a manner that they are retained in a usefully stable form until the tablet is ready for use. The tablets of the present invention are prepared by careful control of the particle sizes and surface treatments of selective components as hereinafter more fully described and further by careful control of the moisture level during the preparation as well as in the final product. In the tablets so prepared, the enzyme is not detrimentally inactivated during storage and further is readily released on the dissolution of the tablets during use, permitting enzymatic cleansing activity to initiate before the dissolution of the active oxygen compound reaches a level which would totally inactivate the enzyme. Moreover, the effervescence producing composition aids dissolution and provides mechanical cleansing action without significantly impairing the cleansing action of the other components.

In the denture cleaner tablet of the present invention, the enzyme is incorporated in and is present as a finely divided powder, granules or as coated prills, the peroxygen or active oxygen compound as granules and the effervescence producing compositions as coated granules. It is further critical and essential that the incorporation of the active components be carried out in a stepwise manner as hereinafter described. Moreover, the preparation is carried out in such a manner that during manufacture the moisture levels at all times is no greater than about 0.5 percent and thereafter is further reduced in the finished tablet to less than about 0.1 percent, preferably less than 0.05 percent. In the specification and claims when describing the components as being present as powder, granules or within a particular particle size range, reference is being made to the discrete particles which are being added to the tablet formulation and which retain their identity within the gross tablet structure.

The enzyme component of the novel tablets is at least one enzyme which is useful for acting on food, food degradation products, mucin and plaque. A preferred embodiment of the present invention contemplates a tablet in which the enzyme is a proteolytic enzyme. However, the methods for preparing compressed denture cleanser tablets containing both enzyme and active oxygen compounds in which the enzyme is resistant to premature inactivation is applicable to all enzymes including non-proteolytic enzymes such as carbohydrases, lipases, amylases, dextranases, etc. The enzymes may be of plant, animal or microbial origin. Many are available commercially under various trade names and are suitable for the present use.

The enzymes may be in a powdered, granular or prilled form. When it is to be employed as a powder, it is generally of particle size sufficiently small to pass through a No. 200 sieve. Mesh, screen or sieve number as herein employed refers to the number of openings per linear inch as set forth by the U.S. Bureau of Standards and the relationship to particle size is found in standard references such as Remington's Pharmaceutical Sciences, 14th edition, Mack Publishing Company, 1970. Generally speaking, the enzymes of particle size to pass through a No. 200 sieve are about 74 microns ($\mu$) or less in diameter, and may range in size from about 50 microns to about 74 microns. The enzymes are usually available commercially in a suitable particle size having been prepared by spray drying.

Preferably, to provide added stability while in the dry tablet, the enzyme may be granulated or coated with a non-detergent low melting solid, preferably one with a melting or softening point below about 100° F. A preferred coating agent is micronized polyethylene glycol 6000 (polyethylene glycol with average molecular weight of 6000). When employed as granules or prills, the particle size is no greater than that which will pass through a No. 20 sieve. Prills may be formed employing the foregoing polyethylene glycol 6000 and prilling by conventional procedures.

The peroxygen or active oxygen component of the tablet is of at least one compound which forms hydrogen peroxide or nascent oxygen when placed in solution. It is to be distinguished from other oxidizing agents such as those which form hyprochlorite ion or chloride and which are frequently present in denture cleansing compositions. This distinction is important since the latter has been found to inactivate the enzyme on dissolution and are therefore not contemplated as the oxidizing agent in the instant denture cleanser tablets. In this connection, it is to be noted that inorganic chlorides such as sodium chloride which forms hypochlorite in the presence of peroxygen compounds are also to be avoided. Suitable active oxygen compounds include sodium peroborate monohydrate and tetrahydrate, potassium persulfate, sodium carbonate peroxide, diperisophthalic acid, potassium peroxydiphosphate, and sodium aluminum aminohydroperoxide.

The peroxygen or active oxygen component must be in a granular form and of particle size such as to be retained by a No. 200 sieve. Thus, it is larger than about 74 microns but no greater than about 840 microns, i.e., it passes through a No. 20 sieve.

The effervescence producing composition is a carbon dioxide generating mixture comprising a carbonate compound and an acid. By "carbonate compound" is meant an alkali metal carbonate or bicarbonate, such as for example carbonate or bicarbonate of sodium or potassium. The acid component is preferably citric or tartaric acid or mixtures thereof but may be other water soluble acids including mixtures thereof such as, for example, sodium or potassium acid phosphates, gluconic acid, malic acid, etc. The acid and the carbonate compound are generally employed in approximately stoichiometric amounts although a very slight excess of acid may be employed to effectively generate the potential carbon dioxide. Large excesses of acid are generally not desirable especially if the enzyme has an optimum pH in the neutral range as is the case with most proteases.

The effervescence producing composition is employed in a granular coated form. It is contemplated that some of each essential component of the effervescence producing composition, namely the acid and the carbonate compound are present in each discrete particle of the granules. By granular form is meant of particle size to pass through a No. 16 sieve but be retained at least by a No. 100 sieve (about 149 microns) and generally in the range of particles passing through a No. 20 (about 840 microns) sieve but retained by a No. 70 sieve (about 210 microns). The preparation of the granules and the desired coating thereof may be accomplished simultaneously. Preferred coating agents are the polyvinylpyrrolidones, particularly those of K-values (Fikentscher's viscosity coefficient) in the range of 26 to 32, which may further function as binders in tablet formation. The preparation of the coated, granular effervescence producing composition may be carried out as a first step in the tablet producing procedure or may be carried out as a prior separate step. Moreover, the preparation may be modified to provide for inclusion of the enzyme during the granulation step; it is not permissible to include both enzyme and active oxygen compound in the granulation step.

A component which has no cleansing function but is necessary to provide the desirable properties and further is necessary in tablet preparation is a lubricant. In the preparation of the tablets of the present invention water-soluble lubricants are contemplated and the preferred lubricant is a two component system having as components (a) magnesium lauryl sulfate in the form of a dry powder having an average particle size ranging from about 12 to about 20 microns, preferably about 16 microns and (b) micronized polyethylene glycol of average molecular weight in the range 6,000 to 20,000 and which is the subject matter of application Serial No. 482,403, filed June 24, 1974. Alternatively, magnesium lauryl sulfate alone may be employed.

Generally, for better cleaning purposes, a minor amount of surfactant is included. Suitable surfactants include anionic water-soluble salts of organic sulfoxy compounds having in their molecular structure an alkyl or acyl radical of carbon content within the range of about 8 to 18. Representative groups are alkali metal alkyl sulfates, sulfoacetates and benzenesulfonates. A preferred surfactant is sodium lauryl sulfoacetate.

In addition, certain optional ingredients may be incorporated. Generally, an indicator dye and a flavor ingredient are included. In addition, anti-foam agent may be added. Since a completely water-soluble tablet is contemplated, insoluble fillers and nonessential ingredients other than the foregoing are avoided.

Suitable dyes for inclusion in the tablets are those which are readily oxidized by the peroxygen compound in about fifteen to thirty minutes and may be one having cyclohexadienimine nucleus and available as FD&C Green #1 (Guinea Green B), FD & C Blue #2, or other dyes including azo dyes. Suitable flavoring include spray dried powders of peppermint and others flavor oils conventionally employed in dental preparations. All components, essential or optional, are employed in a purity appropriate for pharmaceutical use and are readily available commercially.

The amounts of the active components will vary depending on the particular enzyme, active oxygen compound, acid and carbonate compound. When broadly expressed as weight of component per total weight of tablet, it may be found to lie within the following ranges: the enzyme from about 0.8 to 3.5 percent; the active oxygen compounds from about 30 to 50 percent; the effervescence producing composition comprising an acid and an alkali metal carbonate compound from about 45 to 65 percent. More specifically, the enzyme is employed in an amount of from about 25 mg to 50 mg per 3 gram tablet. The active oxygen component may be supplied as a single active oxygen compound or as a mixture (usually two) of active oxygen compounds. Since different active oxygen compounds supply different amounts of active oxygen, the amount of compound or compounds employed is usually that sufficient to supply active oxygen in an amount of from about 3.5 percent to about 4.5 percent by weight based on the weight of final tablet. In the effervescence producing composition, the acid or acids and carbonate compound are employed in substantially stoichiometric amounts and the amounts employed are such sufficient to produce about 8 to 12 millimoles of carbon dioxide or about 11 to 18 percent by weight of carbon dioxide by weight of tablet. It is contemplated that this may be accomplished by providing at least about 45 percent of the total weight of the tablet to be of the effervescence producing composition. This is essential for rapid disintegration of the tablet to occur prior to substantial release of the peroxygen compound.

In addition, the amount of acid to be included in the effervescence producing composition must be selected with consideration of the pH of the solution resulting when the tablet is dissolved in water. Failure to observe this consideration may result in premature deactivation of the enzyme. The formulations should be adjusted so that on dissolution of the tablet, the pH is in the range for optional enzyme activity of the particular enzyme used. In the case of a neutral protease, the optimum pH range is from about pH 6.0 to about pH 7.5.

The other components may be employed in amounts hereinafter designated. The polyvinylpyrrolidone coating agent is employed in such amounts as to constitute about 0.5 to 1 percent of the tablet weight. It is employed by initially admixing with the effervescence producing composition to produce coated granules and the amount employed for this initial mixing is from 1 to 2 percent by weight of the granules.

The amount of water-soluble lubricant employed may be up to 5 percent, preferably, in the range of from about 0.5 to 1 percent by weight of the tablet. When the lubricant is the preferred lubricant system comprising magnesium lauryl sulfate powder and micronized polyethylene glycol 6000, the amount of the former is in the range of from about 0.1 to 0.3 percent and the latter in the range of from about 0.2 to 0.4 percent. Alternatively, magnesium lauryl sulfate alone may be employed and the amount is essentially the same as the amount employed with the polyethylene glycol.

Surfactants when added to improve wetting properties usually do not constitute more than about 3 percent of the total weight of tablet. Preferably, small amounts are added, usually in the range of from about 0.5 to 1 percent.

Spray dried powder flavoring, when employed, may be added in amounts of from about 1 to 3 percent. Dyes or coloring, if employed, are usually in the range of from about 0.05 to 0.1 percent. A water-soluble dye system may be usefully employed as a timing indicator of cleaning accomplished. Thus, a dye system with a fade time of 12 to 15 minutes could be employed to indicate substantial completion of cleaning of the denture. All optional ingredients constitute no more than about 3 percent of the total weight of tablet and are contemplated to be completely water-soluble.

The denture cleanser tablets may be produced by first preparing a coated granular effervescence producing composition comprising an acid and a carbonate compound mixture by adding thereto a solution of polyvinylpyrrolidone, drying to the desired moisture content, screening to the appropriate particle size; thereafter blending the coated granular effervenscence producing composition so prepared with appropriately dried enzyme, active oxygen compound, and other components, and finally, adding a water-soluble tablet lubricant or lubricant system, compressing into tablets and drying to the critical moisture level. In order to achieve denture cleanser tablets having the desired properties, substantial departure from the foregoing steps in the preparation should be avoided. Thus, it is critical and essential that all components not be intermixed during the granulation procedure. The tablets may then be packaged for subsequent use for effectively cleaning stained and soiled dentures.

A preferred method for preparing the denture cleanser tablets is in the following stepwise manner. As an initial step, an effervescence producing composition in the form of coated granules is prepared by dissolving polyvinylpyrrolidone in alcohol solution that can be 50% aqueous to completely anhydrous, preferably 190 proof ethyl alcohol, and adding it to a dry pre-blended mixture of acid and carbonate compound (optionally pre-blended with a dye) and thoroughly blending the resulting mixture for several (3 to 5) minutes to form a granular coated effervescent composition. The wet granular mass is dried to a moisture level no greater than about 0.5 percent. This is conveniently accomplished by drying in a forced air oven at temperatures in the range of about 45° to 55° C., preferably at about 50° C. for about 15 to 18 hours. The dried mass is then screened to obtain a granular coated effervescence producing composition of particle size that will pass through a No. 16 sieve. The granules may be immediately employed in the next step or stored for future use.

In the next step, the essential enzyme and active oxygen compound cleansing components as well as remaining components are combined with the granular, coated effervescence producing compositions. This is carried out by adding to the screened mass at least one active oxygen compound, at least one enzyme, a surfactant and if employed, flavoring and other optional ingredients and blending the resulting mixture, usually for about 15 to 25 minutes. It is critical and essential for the moisture level in this step to be no greater than about 0.5 percent and care is taken to employ components which have been dried previously to at least this level of dryness. Thereafter, the cleansing composition are formed into tablets by first adding to the mixture a water-soluble lubricant or lubricant system, preferably the latter as a dry powdered magnesium lauryl sulfate and micronized polyalkylene glycol mixture, blending the resulting mixture for about 5 to 10 minutes, and then feeding into a tablet press and compressing into tablets. The tablets are then dried to a moisture content of no greater than 0.1% and preferably of less than 0.05%. This is conveniently accomplished by drying in a forced air oven in the range of from about 175° to 185° F., preferably about 180° F. for from 2 to 4 hours. In the tablets thus prepared, the effervescence producing composition, the enzyme and the peroxygen compound retain their identity within the gross tablet structure. Moreover, surprisingly, useful enzyme activity is not lost during this terminal drying step and thus each component of the tablet is capable of performing its intended function.

The preparation of the coated effervescence producing granules may be carried out as a prior separate operation although carrying out the preparation as an initial step in the tablet forming procedure is preferred. The coating agent preferably is prepared by dissolving the coating agent, polyvinylpyrrolidone, in about 95 percent aqueous alcohol. Although ethanol is preferred, isopropyl alcohol may be employed in the coating and granulation step. Also, although 95 percent (190 proof) alcohol is preferred, anhydrous (200 proof) alcohol may be employed, and further, in small batch preparations even 50 percent aqueous alcohol may be employed without adverse effect on formation of the coated granules provided the mixing time is no more than three minutes and there is appropriate drying of the granules prior to use in subsequent tablet formation. The concentration of the polyvinylpyrrolidone therein is generally in the range of 20 to 30 percent (weight by volume). A 20 to 25 percent solution in 190 proof ethanol is preferred.

The enzyme may be precoated with a water-soluble wax such as polyethylene glycol 6000. If the enzyme is employed in a coated form, the coated enzyme may be prepared by blending the dry enzyme or enzymes and polyethylene glycol 6000 or other water-soluble wax for about 10 minutes. Preferably it is prilled by blending with molten low melting wax and forcing the melt through a nozzle of a size to produce prills which will pass through a No. 20 sieve. Precoating of enzymes unexpectedly have been found to be unessential provided that the stepwise procedure is observed during the preparation of the tablet and the critical drying steps are not overlooked.

The effervescent enzyme and active oxygen containing denture cleanser tablets prepared as described are employed to clean dentures by placing in water with the denture to be cleaned for time sufficient to effect the desired cleaning. The tablets may be from about 2.5 to 3.5 grams in total weight and are usually employed with warm water, preferably initially about 100° to 120° F. in an amount sufficient to completely cover the denture. Generally this amounts to from about 60 to 180 milliliters or 2 to 6 ounces. When so employed, effective and desired cleaning may be achieved in about 15 to 20 minutes but in more highly stained dentures, longer periods may be desirable. The tablets when thus employed are found to effectively remove mucin, plaque, berry and grape stains not readily removed by tablets not containing enzymes. The tablets of the present invention also removes coffee, tea and other stains. Moreover, this is accomplished without brushing and usually without the overnight soaking necessary with the generally available tablets. Thus, unexpectedly the desired enzyme activity is not detrimentally affected by the active oxygen compounds in the denture cleanser tablets prepared according to the present invention.

The following examples illustrate the invention but are not to be construed as limiting:

EXAMPLE I

A coated effervescent composition is prepared first by dry blending 739 grams of anhydrous citric acid powder, 897 grams of granular sodium bicarbonate (Church and Dwight #5, of particle size to be retained on No. 170 sieve), 2.7 grams of Guinea Green B (dye), and 0.1 gram of D & C Yellow No. 10 (dye). To the blend is added a previously prepared solution of 30 grams of polyvinylpyrrolidone (K 29-32; the K value is calculated from a measurement of the relative viscosity of the polymer and the average molecular weight of the polymer is readily obtainable therefrom) in 40 milliliters of a 50 percent aqueous solution of 190 proof ethanol and mixing for about 3 minutes, thereafter drying about 16 hours in a forced draft oven at 50° F., and finally screening through a No. 16 screen.

The screened coated granular effervescent composition thus prepared is placed in a twin shell blender and there is added thereto 555 grams of granular sodium perborate monohydrate, 689 grams of granular potassium monopersulfate, 63.6 grams of spray dried peppermint flavor, 20 grams of sodium lauryl sulfoacetate, and 25 grams of bacterial protease of 3 Anson Units (activity based on tyrosine released from hemoglobin as substrate) and the resulting mixture blended for about 15 minutes. Thereafter, 5.13 grams of magnesium lauryl sulfate and 10.25 grams of micronized polyethylene glycol (av. m.w. 6000) are added, the mixture blended for about 5 minutes and then fed into the hoppers of a tabletting press where they are compressed into one thousand, ⅝ inch diameter, 3.05 gram tablets having a Stokes hardness of 13 kilograms.

The tablets are then dried at about 180° F. for about 2 hours in a forced air oven to reduce the moisture from about 0.36 percent to 0.03 percent and are then strip packaged in 1 mil hermetic foil packets.

The tablets thus prepared are effective in removing oral deposits such as plaque, food particles and stains which tend to accumulate on dentures. The cleaning properties may be seen employing stained acrylic plates as models for stained dentures.

The stained acrylic plate models are prepared by applying via an aerosol spray to the surface of roughened acrylic plates a well-beaten mixture employing 120 grams egg yolks, 12 grams of grape juice concentrate, and 8 grams burnt sugar coloring. The sprayed plates are heated for two hours at 50° C. to set the stain.

In determinations for the effectiveness of the tablets of the present invention, the plates are placed in 180 milliliters of tap water at 110° F. and the tablets individually dropped therein wherein bubbles begin to evolve immediately with complete dissolution of the tablet within about 90 seconds. The pH of the solution is approximately 6.2–6.3. Observation of the plates after 15 minutes shows that from about 70 to about 95 percent stain removal may be obtained.

EXAMPLE II

In an operation carried out in a manner similar to that described in Example I, an effervescent composition first is prepared in a granular form from the following formulation:

| Component | Amount |
| --- | --- |
| Citric acid (anhydrous) | 92.4 kg |
| Sodium bicarbonate (Church & Dwight No. 5) | 112.1 kg |
| Guinea Green B (green dye) | 336.2 g |
| D & C Yellow No. 10 (yellow dye) | 12.5 g |
| Polyvinylpyrrolidone (K 29–32) | 3,750.0 g |
| 190 proof alcohol | 16.0 liters |

The preparation is carried out by (1) preblending the green and yellow dyes with 10 kilograms each of citric acid and sodium bicarbonate, (2) admixing the preblend with the remaining citric acid and sodium bicarbonate at high speed in a production size Day Pony mixer for about five minutes, (3) adding thereto over a period of about one minute a solution of the polyvinylpyrrolidone in alcohol and continuing the stirring for an additional 3 minutes, and (4) drying for 16 hours at 50° C.

Tablets are prepared employing two lots of granules prepared as above described together with the components listed below:

| Component | Amount |
| --- | --- |
| Bacterial protease (3 Anson Units) | 6,250.0 g. |
| Peppermint flavoring | 15.9 kg |
| Sodium perborate monohydrate | 138.7 kg |
| Potassium monopersulfate | 172.2 kg |
| Sodium lauryl sulfoacetate | 5,000.0 g. |
| Magnesium lauryl sulfate | 1,281.2 g. |
| Polyethylene glycol 6000, micronized | 2,562.5 g. |

The tablet preparation is carried out by (1) placing in a 30 cubic foot twin shell blender the two lots of effervescent composition granules after first screening through a No. 10 screen, (2) adding thereto the enzyme, flavoring, surfactant and the active oxygen compounds and blending for 15 minutes, (3) adding to the resulting mixture micronized polyethylene glycol 6000 and magnesium lauryl sulfate (pre-sieved through a No. 40 sieve) and blending for 5 minutes, and (4) compressing into 125,000 tablets. The tablets are dried for 4 hours at 80° C. in a forced air oven with 750 feet per minute air velocity and then strip packaged in hermetic foil packets.

EXAMPLE III

Tablets prepared in a manner described in Example II are subjected to aging at room temperature and accelerated aging by maintaining at temperatures of 100° F. and 120° F. for 1 month. At the end of this period, the tablets are examined for cleansing effectiveness by conducting duplicate stain removal studies on acrylic plates in a manner similar to that described in Example I. For comparative purposes, a tablet similar in composition but not containing enzyme ("Placebo") and a commercially available non-enzyme denture cleanser tablet, similarly aged at room temperature are also examined for cleansing effectiveness.

The results are as follows:

TABLE I

| Tablet | Percent Stain Removal Average of Two Results |
| --- | --- |
| Aged at room temperature (~70° F.) | 78.6% |
| " 100° F. | 75.3% |
| " 120° F. | 65.2% |
| Placebo | 23.9% |
| Commercial Tablet | 24.6% |

EXAMPLE IV

Tablets prepared in a manner similar to that described in Example II are highly effective in the removal of coffee and tea stains as seen by tests carried out by placing a tablet in 125 milliliters of water 115°–120° F., placing therein acrylic tiles previously stained with coffee or tea and making observations at 15 minute and overnight intervals. The average results of observations and judging by seven separate panel members are seen in Table II.

The test tiles employed are approximately 1"×1" of acrylate commonly used in dentures and are stained prior to the test by placing the tiles in a concentrated coffee or tea solution, heating for 6 to 8 hours at 180°–200° F., followed by maintaining it at 80° C. for sixteen hours to set the stain.

TABLE II

| Stained Substrate & Time of Immersion | Percent Stain Removal |
| --- | --- |
| Coffee, 15 minutes | 91 |
| Coffee, overnight | 97 |
| Tea, 15 minutes | 78 |
| Tea, overnight | 97 |

EXAMPLE V

Tablets prepared in the manner described in Example II are employed in tests to determine effectiveness in removing heat set egg yolk-blueberry stain from acrylic plate surfaces and compared with non-enzyme containing commercial tablet denture cleansers. The test simulates effectiveness in removal of blueberry stain locked in plaque on the surfaces of acrylic dentures.

For the test, three pronged acrylic plates are employed, each prong being about 2¾ inch×3 inch and previously roughened to a non-reflecting matte finish. Each prong is sprayed uniformly with an aerosol spray of an egg yolk-blueberry stain prepared by blending to a syrup, 120 grams of egg yolk, 12 grams of blueberry pie filling and 8 grams of burnt sugar coloring, then admixing 66 grams of the syrup with 132 grams of water to a uniform dispersion and thereafter appropriately filling and charging in an aerosol spray can. The sprayed plates are placed in a forced air oven (51 feet per minute) at 50° C. for 2 hours to set the stain.

In the test, each prong is placed in a separate container filled with 200 milliliters of tap water at 100° F. To one container there is placed a tablet prepared as described in Example II and to each of the other containers are placed different commercial non-enzyme containing denture cleanser tablets identified as Commercial Tablet A and Commercial Table B. The plates are allowed to soak for 15 minutes, then rinse dipped in the soak solutions and drained. The plates are then examined visually to determine the percent stain removed. The average results of five tests are as follows:

TABLE III

| Tablet | Percent Stain Removed |
| --- | --- |
| Example II | 91.1 |
| Commercial Tablet A | 15.7 |
| Commercial Tablet B | 13.3 |

EXAMPLE VI

Employing tablets prepared in a manner described in Example II and aged by maintaining at 70° F. for six months as well as freshly prepared tablets and commercially available non-enzyme containing tablets, quantitative tests are conducted to determine effectiveness in removal of locked-in blueberry stain from acrylic plates.

Blueberry-egg yolk stain prepared as described in Example V are sprayed onto weighed acrylic plates (2"×4") the surfaces of which are previously roughened to a nonreflective matte finish with carborundum paper. After heat setting the stain as previously described, the plates are weighed to find the net weight of stain. The plates are soaked for 15 minutes in test solutions prepared by separately dissolving the tablets in 180 ml. of 110° F. tap water. The plates are then removed, dried and reweighed. After correcting for weight of stain on the portion of plate not immersed, percent stain removed is determined. The mean results of five tests for aged, unaged and non-enzyme commercial tablets are seen in TABLE IV:

TABLE IV

| Tablet | Percent Stain Removed |
| --- | --- |
| Example IV (Aged) | 94.0 |
| Commercial Tablet A | 27.5 |
| Commercial Tablet B | 40.9 |
| Example IV (Not Aged) | 94.0 |

The denture cleanser tablet described in the foregoing examples merely illustrates one of the preferred combination of ingredients, and other ingredients previously described may be substituted for one of the foregoing or may be included additionally within the limitations previously set forth. Moreover, the amounts by weight of the ingredients in the preferred combination may be expressed in terms of weight based on the weight of the final tablet as follows:

(1) an enzyme, about 0.8 to 1.6 percent;
(2) sodium perborate monohydrate, about 13 to 22 percent, and potassium persulfate, about 17 to 29 percent;
(3) citric acid powder, about 20 to 30 percent,
(4) granular sodium bicarbonate, about 25 to 35 percent;
(5) sodium lauryl sulfoacetate, about 0.5 to 1 percent;
(6) polyvinylpyrrolidone, about 0.5 to 1 percent,
(7) magnesium lauryl sulfate powder, about 0.1 to 0.3 percent, and micronized polyethylene glycol (average m.w. 6000), about 0.2 to 0.4 percent.

In addition, dyes, flavoring, etc., may be included. Amounts of such other components generally do not exceed about 3 percent of the total weight of the tablet.

What is claimed is:

1. A stable, water-soluble denture cleanser tablet providing enzymatic and active oxygen cleansing action consisting essentially of
   (a) from about 0.8 to about 3.5% by weight of a neutral bacterial protease enzyme of about 3 Anson Units activity;
   (b) from about 30 to about 50% by weight of at least one active oxygen compound which is selected from the group of peroxygen compounds which form hydrogen peroxide or nascent oxygen when placed in solution and is further selected from the group consisting of sodium perborate monohydrate, sodium perborate tetrahydrate, potassium persulfate, sodium carbonate peroxide, diperisophthalic acid, potassium peroxydiphosphate and sodium aluminum aminohydroperoxide;
   (c) from about 45 to about 65% by weight of at least one effervescence-producing composition which is selected from the group of carbon dioxide generating mixtures consisting essentially of at least one water-soluble organic acid selected from the group consisting of citric acid, tartaric acid, gluconic acid and malic acid and at least one alkali metal carbonate compound selected from the group consisting of sodium bicarbonate, potassium bicarbonate, sodium carbonate and potassium carbonate; and
   (d) from about 0.1 to about 5% by weight of at least one water-soluble lubricant selected from the group consisting of magnesium lauryl sulfate and a mixture of magnesium lauryl sulfate and polyethylene glycol having a molecular weight of from about 6000 to about 20,000;
wherein said tablet has a moisture content not greater than about 0.1 percent based on the total weight of the tablet and upon dissolution in an aqueous medium has a pH of from about 6.0 to about 7.5.

2. A tablet according to claim 1 wherein the active oxygen compound is at least sodium perborate monohydrate.

3. A tablet according to claim 1 wherein the active oxygen compound is at least potassium persulfate.

4. A tablet according to claim 1 wherein the water-soluble organic acid is at least citric acid.

5. A tablet according to claim 1 wherein the water-soluble organic acid is at least tartaric acid.

6. A tablet according to claim 1 wherein the alkali metal carbonate compound is at least sodium bicarbonate.

7. A tablet according to claim 1 wherein the alkali metal carbonate compound is at least sodium carbonate.

8. A tablet according to claim 1 wherein the lubricant is a mixture of magnesium lauryl sulfate and polyethylene glycol having a molecular weight of from about 6000 to about 20,000.

9. A method for cleaning dentures which comprises placing a water-soluble denture cleanser tablet and the denture to be cleaned in an amount of water sufficient to completely cover said denture and for a time sufficient to effect the desired cleaning; wherein said tablet provides enzymatic and active oxygen cleansing action and consists essentially of:
- (a) from about 0.8 to about 3.5% by weight of a neutral bacterial protease enzyme of about 3 Anson Units activity;
- (b) from about 30 to about 50% by weight of at least one active oxygen compound which is selected from the group of peroxygen compounds which form hydrogen peroxide or nascent oxygen when placed in solution and is further selected from the group consisting of sodium perborate monohydrate, sodium perborate tetrahydrate, potassium persulfate, sodium carbonate peroxide, diperisophthalic acid, potassium peroxydiphosphate and sodium aluminum aminohydroperoxide;
- (c) from about 45 to about 65% by weight of at least one effervescence-producing composition which is selected from the group of carbon dioxide generating mixtures consisting essentially of at least one water-soluble organic acid selected from the group consisting of citric acid, tartaric acid, gluconic acid and malic acid and at least one alkali metal carbonate compound selected from the group consisting of sodium bicarbonate, potassium bicarbonate, sodium carbonate and potassium carbonate; and
- (d) from about 0.1 to about 5% by weight of at least one water-soluble lubricant selected from the group consisting of magnesium lauryl sulfate and a mixture of magnesium lauryl sulfate and polyethylene glycol having a molecular weight of from about 6000 to about 20,000;

wherein said tablet has a moisture content not greater than about 0.1 percent based on the total weight of the tablet and upon dissolution in an aqueous medium has a pH of from about 6.0 to about 7.5.

* * * * *